(12) United States Patent
Kabrick (10) Patent No.: US 7,758,825 B2
(45) Date of Patent: Jul. 20, 2010

(54) TRAY REMOVAL HANDLE

(75) Inventor: Chris R. Kabrick, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 1014 days.

(21) Appl. No.: 11/502,201

(22) Filed: Aug. 10, 2006

(65) Prior Publication Data

US 2007/0034544 A1 Feb. 15, 2007

Related U.S. Application Data

(60) Provisional application No. 60/707,140, filed on Aug. 10, 2005.

(51) Int. Cl.
| | |
|---|---|
| A61L 2/00 | (2006.01) |
| A61L 9/00 | (2006.01) |
| B65D 69/00 | (2006.01) |
| B65D 83/10 | (2006.01) |
| B65D 21/00 | (2006.01) |
| B65D 25/10 | (2006.01) |
| A61B 17/06 | (2006.01) |
| A61B 17/08 | (2006.01) |
| A61B 1/00 | (2006.01) |
| A47G 19/00 | (2006.01) |
| A61M 1/00 | (2006.01) |

(52) U.S. Cl. ............ 422/300; 422/1; 422/297; 422/303; 422/305; 206/570; 206/363; 206/514; 206/560; 206/63.3; 206/438; 206/303; 206/388; 206/65; 206/229; 220/457; 220/306; 220/408; 220/575; 220/754; 606/151; 606/153; 606/154; 606/155; 606/156; 604/319; 600/133; D9/737; D9/414

(58) Field of Classification Search ............ 422/1, 422/297, 300, 303, 305; 206/570, 363, 514, 206/560, 63.3, 438, 303, 388, 65, 229; 220/457, 220/306, 408, 575, 754; 606/151, 153–156; 604/319; 600/133; D9/737, 414
See application file for complete search history.

(56) References Cited

U.S. PATENT DOCUMENTS 4,522,302 A 6/1985 Paikoff (Continued)

FOREIGN PATENT DOCUMENTS

WO WO 87/05278 * 9/1987

*Primary Examiner*—Jill Warden
*Assistant Examiner*—Monzer R Chorbaji
(74) *Attorney, Agent, or Firm*—Brinks Hofer Gilson & Lione (57) ABSTRACT

A handle assembly facilitates the removal of a sterile inner tray containing sterile medical instruments from a medical kit during an OR procedure. The handle assembly may have a handle coupled with an elongated member having a male end and a female end. The inner tray may be wrapped in medical packaging. Subsequently, the elongated member may be wrapped around the inner tray and the male and female ends interconnected. The inner tray may be positioned inside of an outer tray. A bacterial barrier may be formed over a portion of the outer tray to enclose the inner tray. The inner tray, including the medical instruments, may then be sterilized by a sterilization process. During an OR procedure, the handle assemble allows a sterile nurse to remove the sterile inner tray from the non-sterile outer tray without making contact with the non-sterile outer tray and/or contaminating the sterile medical instruments.

20 Claims, 8 Drawing Sheets

U.S. PATENT DOCUMENTS

| | | | |
|---|---|---|---|
| 5,165,539 | A | 11/1992 | Weber et al. |
| 5,540,901 | A | 7/1996 | Riley |
| 5,879,620 | A | 3/1999 | Cohen |
| 6,048,503 | A | 4/2000 | Riley et al. |
| 6,116,426 | A | 9/2000 | Slonim |
| 6,257,401 | B1 * | 7/2001 | Mangla et al. .............. 206/204 |
| 6,350,418 | B1 | 2/2002 | Venderpool et al. |
| 6,713,029 | B1 | 3/2004 | Krafft et al. |
| 6,759,017 | B2 | 7/2004 | Wu et al. |
| 6,780,383 | B1 | 8/2004 | Ettlinger et al. |
| 6,800,245 | B1 | 10/2004 | Erbe et al. |
| 6,821,286 | B1 | 11/2004 | Carranza et al. |
| 6,827,913 | B2 | 12/2004 | Wood |
| 6,837,027 | B2 | 1/2005 | Hickey |
| 6,846,305 | B2 * | 1/2005 | Smith et al. ................. 604/410 |
| 6,874,634 | B2 | 4/2005 | Riley |
| 6,910,581 | B2 | 6/2005 | McMichael et al. |
| 6,913,150 | B1 | 7/2005 | Fountain |
| 7,047,994 | B2 * | 5/2006 | McPeak et al. .......... 137/15.24 |
| 2004/0022674 | A1 | 2/2004 | Thurk et al. |
| 2004/0040967 | A1 | 3/2004 | Eiskant et al. |
| 2004/0129595 | A1 | 7/2004 | Dane et al. |
| 2004/0163982 | A1 | 8/2004 | Wilkinson et al. |
| 2004/0200754 | A1 | 10/2004 | Hagemeier |
| 2005/0019237 | A1 | 1/2005 | Riley |
| 2005/0033430 | A1 | 2/2005 | Powers et al. |
| 2005/0191207 | A1 | 9/2005 | Terwilliger et al. |

\* cited by examiner

TRAY REMOVAL HANDLE

PRIORITY AND CROSS-REFERENCE TO RELATED APPLICATION

This application claims priority under 35 U.S.C. §119(e) to provisional application Ser. No. 60/707,140, filed on Aug. 10, 2005, which is incorporated by reference in its entirety herein.

FIELD OF THE INVENTION

The present invention relates to medical instruments. More specifically, the present invention relates to preventing the contamination of sterilized medical instruments.

BACKGROUND

Sterilized medical instruments facilitate the successful performance of numerous medical procedures. However, after a sterilization procedure sterilizes the medical instruments, the sterilized medical instruments should be prevented from becoming contaminated and/or non-sterile until they are used in a medical procedure. One manner by which sterilized medical instruments may be maintained sterile until use is the placement of the sterilized medical instruments into a compact and transferable medical kit. The medical instruments may be manually delivered directly to an operating room for use via the medical kit. For instance, during an operating room (OR) procedure, a circulating or non-sterile nurse may deliver the medical kit to a sterile nurse.

Conventional medical kits may include two primary components: an inner tray acting as a sterilized interior medical instrument holder and a non-sterile outer tray, into which the inner tray may be placed. The inner tray may be configured to hold a number of medical instruments in place. After the medical instruments are placed within the inner tray, the inner tray may be positioned within the outer, larger tray. The inner tray, as well as the accompanying medical instruments, also may be sterilized via a sterilization process.

Additionally, conventional non-sterile outer and sterilized inner trays may each have an upper flange or rim. The outer tray is typically longer, wider, and deeper than the inner tray. However, with the conventional inner and outer trays, the upper rim of the inner tray may leave little or no clearance between the inner and outer trays. Hence, with typical medical kits, it may be difficult for a sterile nurse to remove the sterilized inner tray from the non-sterile outer tray without making contact with the non-sterile outer tray.

SUMMARY OF THE INVENTION

A handle assembly facilitates the removal of a sterilized inner tray containing sterilized medical instruments from a non-sterile outer tray during an operating room or other medical procedure. A circulating nurse may present the sterilized inner tray with the sterilized medical instruments to a sterile nurse by holding the non-sterile outer tray. The handle assembly allows the sterile nurse to remove the sterilized inner tray from the non-sterile outer tray without making contact with the non-sterile outer tray and/or contaminating the sterilized medical instruments.

A medical kit containing sterilized medical instruments includes an outer tray and an inner tray positioned substantially inside of the outer tray, with the inner tray containing one or more medical instruments. The medical kit also includes a handle assembly fastened to the inner tray, the handle assembly having a handle. The handle facilitates the removal of the inner tray from the outer tray.

A handle assembly for a medical kit containing sterilized medical instruments may include a handle and an elongated member coupled with the handle. The elongated member may be manufactured from flexible material and have a male end and a female end, where the male end may be adapted to interconnected with the female end. The handle facilitates the removal of the sterilized medical instruments from the medical kit.

A method of assembling a medical kit includes positioning one or more medical instruments in an inner tray, fastening a handle assembly to the inner tray, the handle assembly having a handle, and positioning the inner tray substantially inside an outer tray, such that the handle facilitates the removal of the inner tray from the outer tray.

Advantages will become more apparent to those skilled in the art from the following description of the preferred embodiments which have been shown and described by way of illustration. As will be realized, the system and method are capable of other and different embodiments, and their details are capable of modification in various respects. Accordingly, the drawings and description are to be regarded as illustrative in nature and not as restrictive.

BRIEF DESCRIPTION OF THE DRAWINGS

The present invention will become more fully understood from the detailed description given herein below and the accompanying drawings which are given by way of illustration only, and are not limitative of the present invention, and wherein.

DETAILED DESCRIPTION OF THE INVENTION

A handle assembly facilitates the removal of sterilized medical instruments located in a sterilized inner tray from a non-sterile outer tray. The handle assembly may include a handle coupled with an elongated member having a male end and a female end. The elongated member may be wrapped around the inner tray and the male and female ends interconnected to secure the handle assembly to the inner tray. Subsequently, the inner tray may be positioned inside of the larger outer tray.

A bacterial barrier may be formed over a portion of the outer tray to enclose the inner tray within the outer tray. The inner tray, including the medical instruments, may then be sterilized by a sterilization process. As a result, during a medical procedure, a circulating nurse may present the sterilized inner tray and the accompanying sterilized medical instruments to a sterile nurse. For instance, the circulating nurse may remove, lift, or peel away the bacterial barrier, or a portion thereof, exposing the sterilized inner tray. Subsequently, the handle assemble may be used by the sterile nurse to remove the inner tray from the non-sterile outer tray without making contact with the non-sterile outer tray and/or contaminating the sterilized medical instruments.

In general, a conventional medical kit may have an inner tray containing medical instruments and an outer tray. The inner tray typically rests within the outer tray. However, there is typically little or no clearance between the inner and outer trays for human fingers. As a result, medical personnel may not easily grab a hold of the inner tray and remove it from the outer tray. Accordingly, the handle assembly disclosed herein facilitates the removal of an inner container and/or medical instruments from an outer container of a medical kit.

Figure 1:
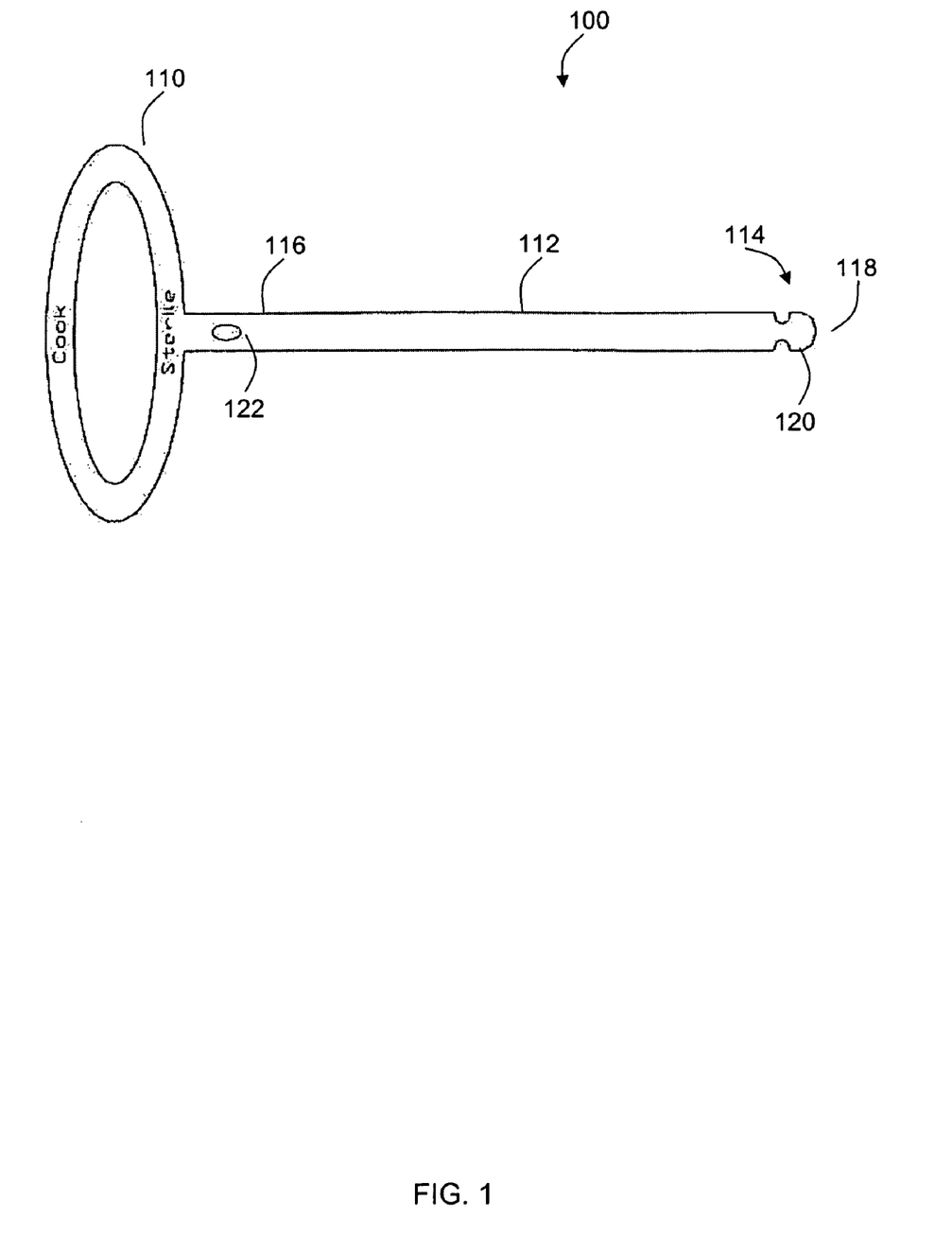
FIG. 1 is an exemplary handle assembly.

FIG. 1 is an exemplary handle assembly 100 that facilitates the removal of sterilized medical instruments from a medical kit without contaminating the instruments. The handle assembly 100 includes two primary components: a handle 110 and an elongated member 112. The handle assembly 100 may include additional, fewer, or alternate components.

In one embodiment, the handle assembly 100 is a single piece. For example, the entire handle assembly 100 may be made from a single manufacturing process, as discussed herein. Alternatively, the each primary component of the handle assembly 100 may be manufactured from a separate manufacturing process and constitute a separate component until integrated with the handle assembly 100.

The handle 110 may facilitate the lifting of a container, such as an inner tray of a medical kit, to which the handle assembly 100 is fastened. The handle assembly 100 may be attached, affixed, tied, secured, or otherwise fastened to the inner tray. For example, the handle assembly 100 may be wrapped around the inner tray.

The handle 110 may have a generally circular shape. Alternate shapes may be used, such as squares or rectangles, or any other shape that provides a grip or a handle. The handle 110 may have a smooth and rectangular exterior. The body of the handle 110 may have a solid, rectangular cross-section. Other types of cross-sections may be used, such as square or circular cross-sections.

The elongated member 112 may be coupled with the handle 110. The elongated member 112 may be slender lengthwise and have a smooth exterior surface. The elongated member 112 may have a rectangular cross-section for the majority of its length. The elongated member 112 may have other shapes and types of exterior surfaces.

The elongated member 112 may be manufactured from a flexible material. The flexible material from which the elongated member 112 is made, either alone or in combination with the shape into which the elongated member 112 is formed, may permit the ends of the elongated member 112 to be brought together in close proximity. As a result, the ends of the elongated member 112 may be firmly affixed or interconnected with one another such that the ends remain together even if a force is applied to the elongated member 112 in a direction that would normally tend to pull the ends apart.

For instance, the ends of the elongated member may be interconnected via a male locking member on one end and a female locking member on the other. Alternatively, the ends of the elongated member may be held together by a clip or other clamping mechanism. The ends of the elongated member may be affixed together with an adhesive or tied together. Other manners of fastening, attaching, securing, affixing, or interconnecting the ends of the elongated member together may be used.

As shown in the example of FIG. 1, a flexible elongated member 112 may have a male end 114 and a female end 116. The male end 114 may have a tip 118 and a corresponding notch 120. The tip 118 may have a smooth exterior and be primarily semi-spherical or semi-circular in shape. The tip 118 may have a convex surface. The tip 118 may have other shapes. For example, the tip 118 may have a generally conical shape and/or culminate at a point.

The notch 120 may be an indentation into the exterior surface of the elongated member 112 in the proximity of the tip 118. The indentation of the notch 120 may have a generally smooth surface and may travel the entire length of the circumference of the elongated member 112. The notch 120 may have a semi-circular shape extending into the body of the elongated member 112 and form a concave surface. Other shapes may be used. For example, the notch 120 may be a square, rectangular or other shaped indention into the exterior surface of the elongated member 112.

Alternatively, the notch 120 may be a protrusion from the exterior surface of the elongated member 112. The protrusion of the notch 120 may have a generally smooth surface. The notch 120 may have a semi-circular shape extending outward from the elongated member 112 and form a convex surface. Other shapes may be used. For example, the notch 120 may be a square, rectangular or other shaped protrusion extending from the exterior surface of the elongated member 112.

The female end 116 may have a slit or narrow opening 122. The opening 122 may be an indentation into the exterior of the elongated member 112. The opening 122 may lead to a cavity inside of the elongated member 112. The cavity may be partially enclosed by one or more edges or flaps of the opening 122.

The elongated member 112 shown in FIG. 1 may be sufficiently flexible to allow the tip 118 of the male end 114 to be inserted into the opening 122 of the female end 116 such that the male end 114 and female end 116 become interconnected. As the tip 118 is inserted into the opening 122, the tip 118 may make contact with and push against the edges of the opening 122. The edges may bend or move to allow the tip 118 to be fully inserted into the opening 122 and/or cavity in the elongated member 112. After the tip 118 is fully inserted into the opening 122, the surfaces of the notch 120 may engage the edges of the opening 122. The interaction between the surfaces of the notch 120 with the surfaces of the opening 122 may operate to lock or interconnect the male end 114 with the female end 116. Alternate mechanisms may be used to interconnect the male end 114 with the female end 116.

The handle assembly 100 may be manufactured from any type of plastic, rubber, polyvinyl chloride (PVC), thermoplastic, or other flexible material. The handle 110 and the elongated member 112 may be manufactured as separate components or as a unitary device. The handle 110 and the elongated member 112 may be manufactured from similar or different materials. In one embodiment, both the handle 110 and the elongated member 112 are manufactured from PETG (glycol-modified polyethylene terephthalate), a copolyester that is a clear amorphous thermoplastic. PETG has high stiffness, toughness, hardness, and impact strength and may be produced in a roll calendaring process similar to that used to make standard PVC. As a result, PETG and PVC have similar temperature resistance, durability, and other characteristics.

The handle assembly 100 may be manufactured from a number of manufacturing processes, such as injection molding, compression molding, heat bonding, dye cutting, or other processes. For example, by dye cutting a sheet of material, such as PETG, virtually any shape and size of the handle assembly 100 may be manufactured. The shape of the handle assembly 100 may include circles, squares, rectangles, angled cuts, or other shapes. The size of the handle assembly 100 may include any width or length.

Similarly, injection molding may mold a handle assembly 100 into virtually any shape and size desired. Injection molding may involve a hot, molten polymer being injected into a cold mold. After the polymer cools and solidifies, the mold is opened and the polymer is ejected in the shape of the cold mold. Likewise, the shape, width, and/or length of the handle assembly 100 also may be variable or customized to the specifications desired if alternate manufacturing processes are used, including the processes mentioned above.

Figure 2:
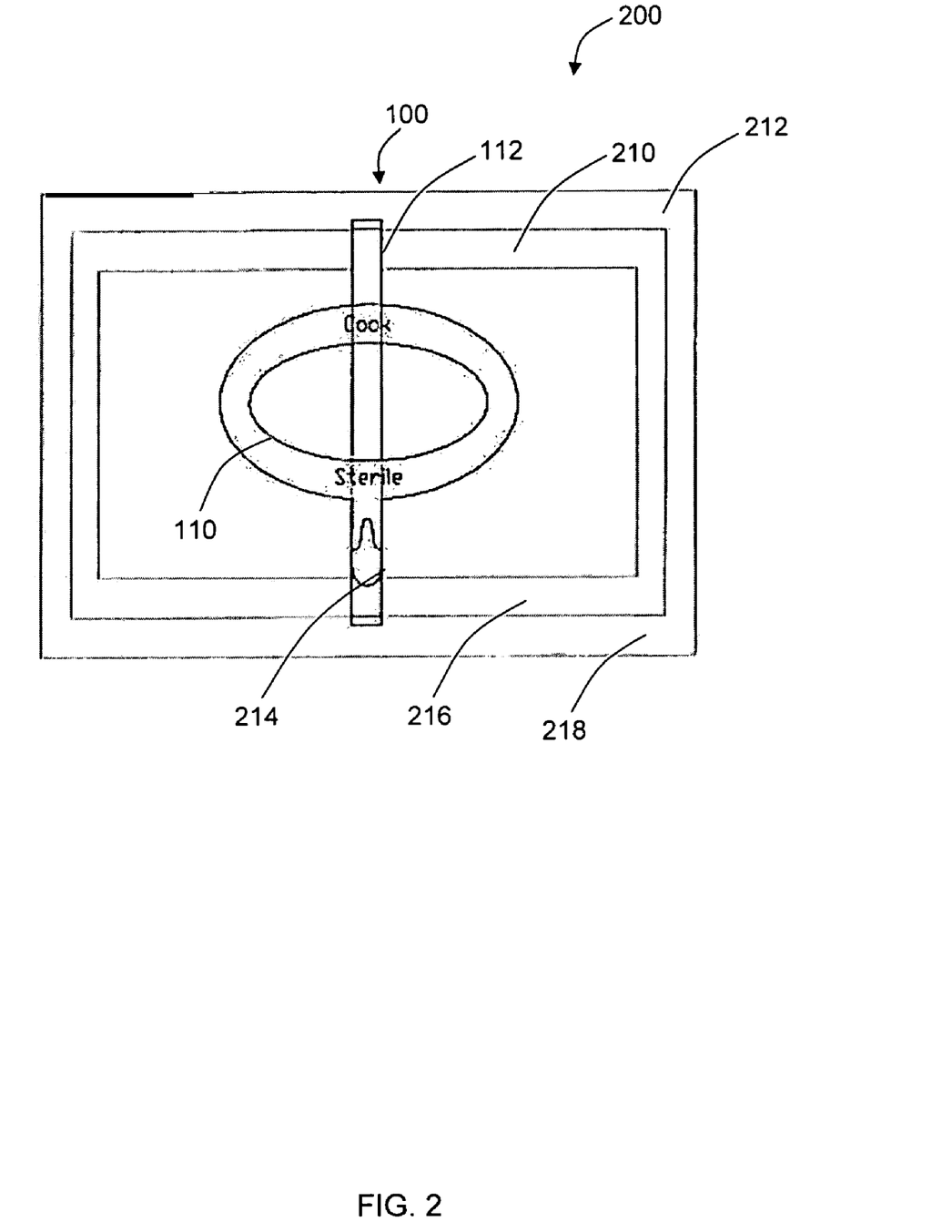
FIG. 2 is an exemplary top view of a medical kit having a handle assembly.

FIG. 2 is shows a top view of a medical kit 200 having a handle assembly 1. The medical kit 200 may include an inner tray 210, an outer tray 212, and the handle assembly 100. The handle assembly 100 may have a handle 110 and an elongated member 112. The medical kit 200 may include additional, fewer, or alternate components.

The inner tray 210 may be a tray or other type of container that holds one or more medical instruments. The outer tray 212 may be a tray or other type of container. The outer tray 212 may be larger than the inner tray 210 such that the inner tray may rest inside of the outer tray 212. For instance, the outer tray 212 may be longer, wider, and deeper than the inner tray 210. The inner tray 210 and the outer tray 212 may be manufactured from a number of different materials and via a number of different manufacturing processes, as discussed in further detail below.

As shown in FIG. 2, the handle assembly 100 may be fastened to the inner tray 100. The handle assembly 100 may be attached, affixed, tied, secured, or otherwise fastened to the inner tray 100. In one embodiment, the handle assembly 100 is secured to the inner tray 100 by wrapping the elongated member 112 around the inner tray 210. The elongated member 112 may be wrapped around the inner tray 210 and the male end of the elongated member 112 interconnected with the female end of the elongated member 112. The interconnection 214 may involve inserting a portion of the male end into a portion of the female end. Other interconnections may be used that include clips, clamps, adhesives, and/or tying the two ends of the elongated member 112 together.

Alternative manners of fastening the handle assembly 100 to the inner tray 210 may be used other than wrapping and interconnecting two ends. For example, the handle assembly 100 may be directly attached, affixed, secured, or otherwise fastened to the inner tray 210. Alternatively, the handle assembly 100 is directly fastened to the inner tray by an adhesive.

The handle 110 may be positioned to be substantially flat against the top of the inner tray 210 after fastening the handle assembly 100 to the inner tray 210. Positioning the handle 110 to be substantially flat against the inner tray 210 may permit a protective layer, film, or other barrier to be placed over the inner tray that encloses the entire handle assembly 100. The connection between the handle 110 and the elongated member 112 may be sufficiently flexible to permit other arrangements between the handle 110 and the inner tray 210.

The handle assembly 100 also may be held in place with respect to the inner tray 210 by being tightly wrapped around the inner tray 210 such that friction exists between the elongated member 112 and the inner tray 210. A snug fit between the elongated member 112 and the corresponding surfaces of the inner tray 210 may prevent substantial slippage of the handle assembly 100 with respect to the inner tray 210 during use, especially while lifting or removing the inner tray 210 from the medical kit 200.

Alternatively, slippage between the handle assembly 100 and the inner tray 210 may be substantially prevented by configuring the inner tray 210 to have one or more notches on its exterior surfaces into which the elongated member 112 fits. For an elongated member 112 having a cubicle body and either a square or rectangular cross-section, the inner tray 210 may have one or more notches having corresponding square or rectangular surfaces. The square or rectangular cross-section of the elongated member 112 may fit snuggly into the one or more notches after the elongated member 112 is wrapped around or otherwise secured to the inner tray 210.

For an elongated member 112 having a tubular body and circular cross-section, the inner tray 210 may have one or more notches having corresponding circular or concave surfaces. The circular cross-section of the elongated member 112 may fit snuggly into the one or more notches after the elongated member 112 is wrapped around or otherwise secured to the inner tray 210. Other shapes may be used for the elongated member 112 and corresponding notches positioned on the inner tray 210.

As shown in FIG. 2, after the handle assembly 100 is wrapped around the inner tray 210, the inner tray 210 may be positioned inside of the outer tray 212. The inner tray 210 may have an upper inner flange or rim 216. The outer tray 212 may have an upper outer flange or rim 218. Both rims 216, 218 may be substantially flat. As the inner tray 210 is positioned inside of the outer tray 212, the inner rim 216 may fit within the outer rim 218. As a result, the inner tray 210 may be come to rest inside of the outer tray 212.

Instead of the notches positioned on the surfaces of the inner tray 210 to prevent substantial slippage between the handle assembly 100 and the inner tray 210, the outer tray 212 may have similar types of notches. The notches on the outer tray 212 may have an interior shape corresponding to the exterior shape of the elongated member 112. For instance, the interior shape may be concave, circular, square, rectangular, or other shapes.

After the inner tray 210 is positioned inside of the outer tray 212, the elongated member 112 may fit into one or more notches on the outer tray 212. As a result, the handle assembly 100 may be substantially prevented from moving with respect to the inner tray 210, at least as long as the inner tray 210 remains positioned inside of the outer tray 212.

In use, the medical kit 200 as shown by FIG. 2 may be placed on a table or held by a circulating nurse. A sterile nurse may then grab a hold of the handle 110 and lift the inner tray 210 out of the outer tray 212. The handle assembly 100 may be strong enough to support the weight of the inner tray 210. The handle 110 may facilitate the removal of the inner tray 210 from the outer tray 212 without the sterile nurse making contact with the outer tray 212.

The inner tray 210, as well as any accompanying medical instruments contained therein, may be sterilized. The outer tray 212 may be non-sterile. Accordingly, the handle 110 may facilitate the removal of sterilized medical instruments from the medical kit 200 without the sterilized medical instruments becoming contaminated.

Figure 3:
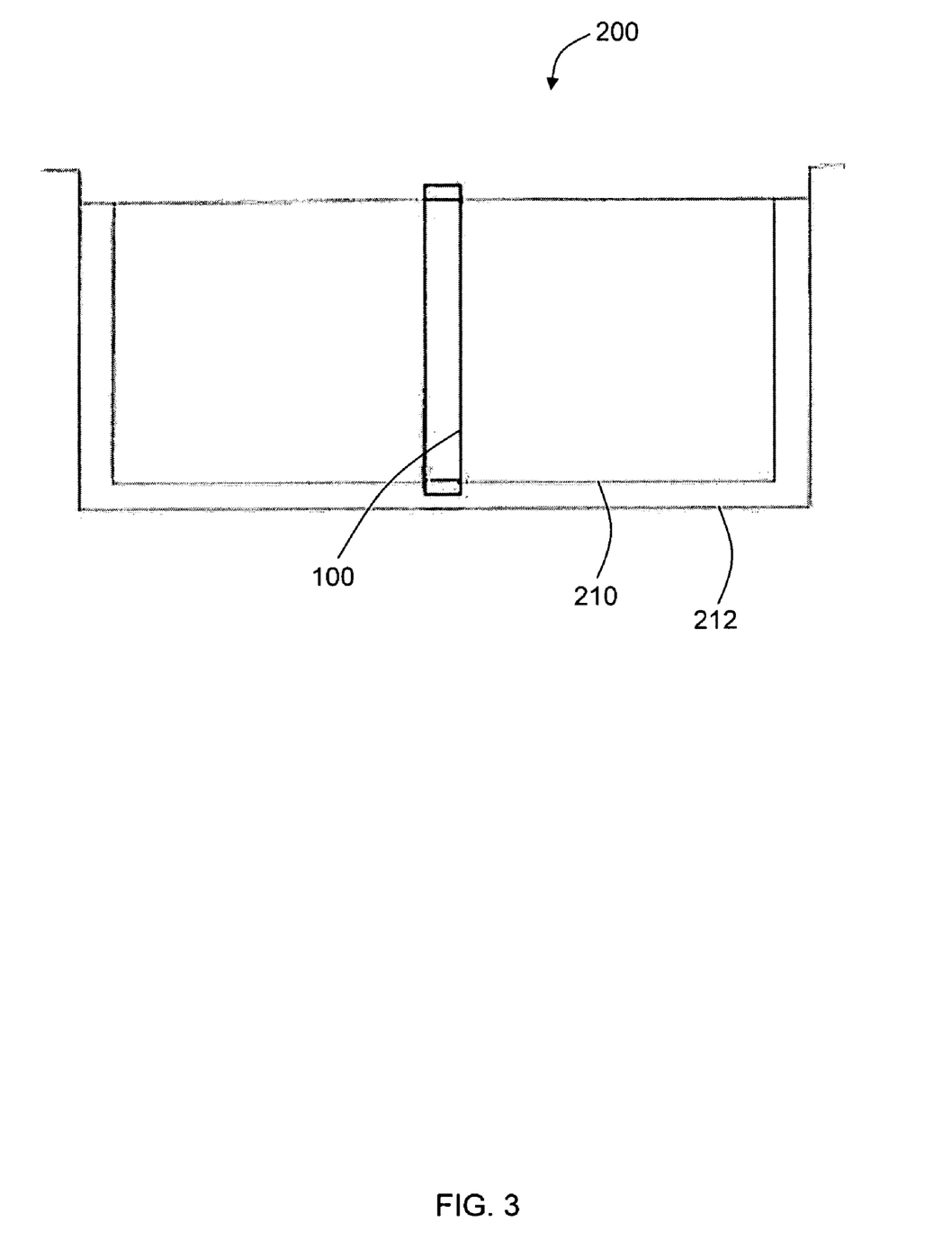
FIG. 3 is an exemplary cross-sectional view of the medical kit shown in FIG. 2.

FIG. 3 is a cross-sectional view of the medical kit 200 shown in FIG. 2. The medical kit 200 may include a handle assembly 100, an inner tray 210, and an outer tray 212. The medical kit 200 may include additional, fewer, or alternate components. The example of FIG. 3 shows that the outer tray 212 is larger than the inner tray 210. The outer tray 212 may be wider, longer, and deeper than the inner tray 210. As a result, when the inner tray 210 is placed substantially inside of the outer tray 212 it may be supported by the inside bottom surface of the outer tray 212. Additionally, the upper inner rim 216 may fit within the inside vertical wall surface 220 of the outer tray 212 such that substantially no clearance exists between the upper inner rim 216 and the inside vertical wall surface 220.

Figure 4:
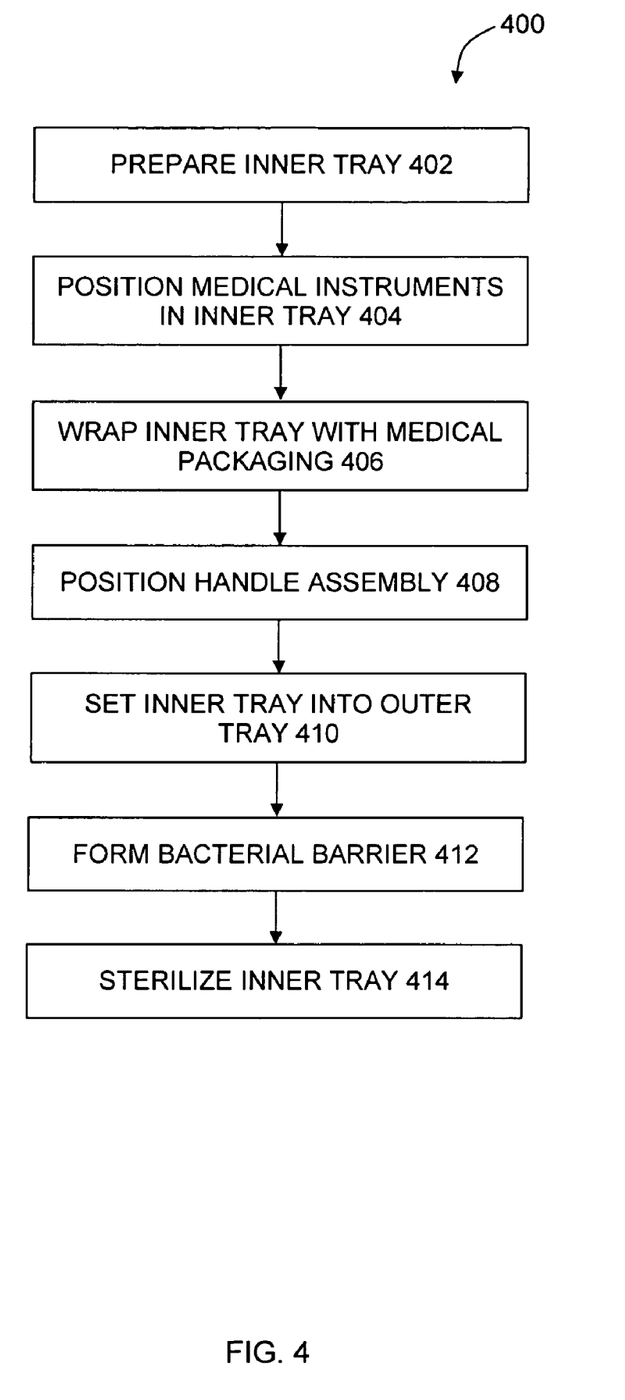
FIG. 4 is a flowchart of an exemplary method of preparing a medical kit having a handle assembly.

FIG. 4 illustrates a method of preparing a medical kit having a handle assembly for the removal of a sterilized inner tray from a non-sterile outer tray. The method may include preparing an inner tray 402, positioning medical instruments in the inner tray 404, wrapping the inner tray with medical packaging 406, positioning the handle assembly with respect to the inner tray 408, setting the inner tray into an outer tray 410, forming a bacterial barrier over the outer tray 412, and sterilizing the inner tray 414. The method may include additional, fewer, or alternate actions.

An inner tray may be prepared 402 to become part of a medical kit. The preparation of the inner tray 402 may include the manufacture of the inner tray. The inner tray may be formed to have a number of crevices and inner surfaces designed to hold a plurality of medical instruments.

Figure 5:
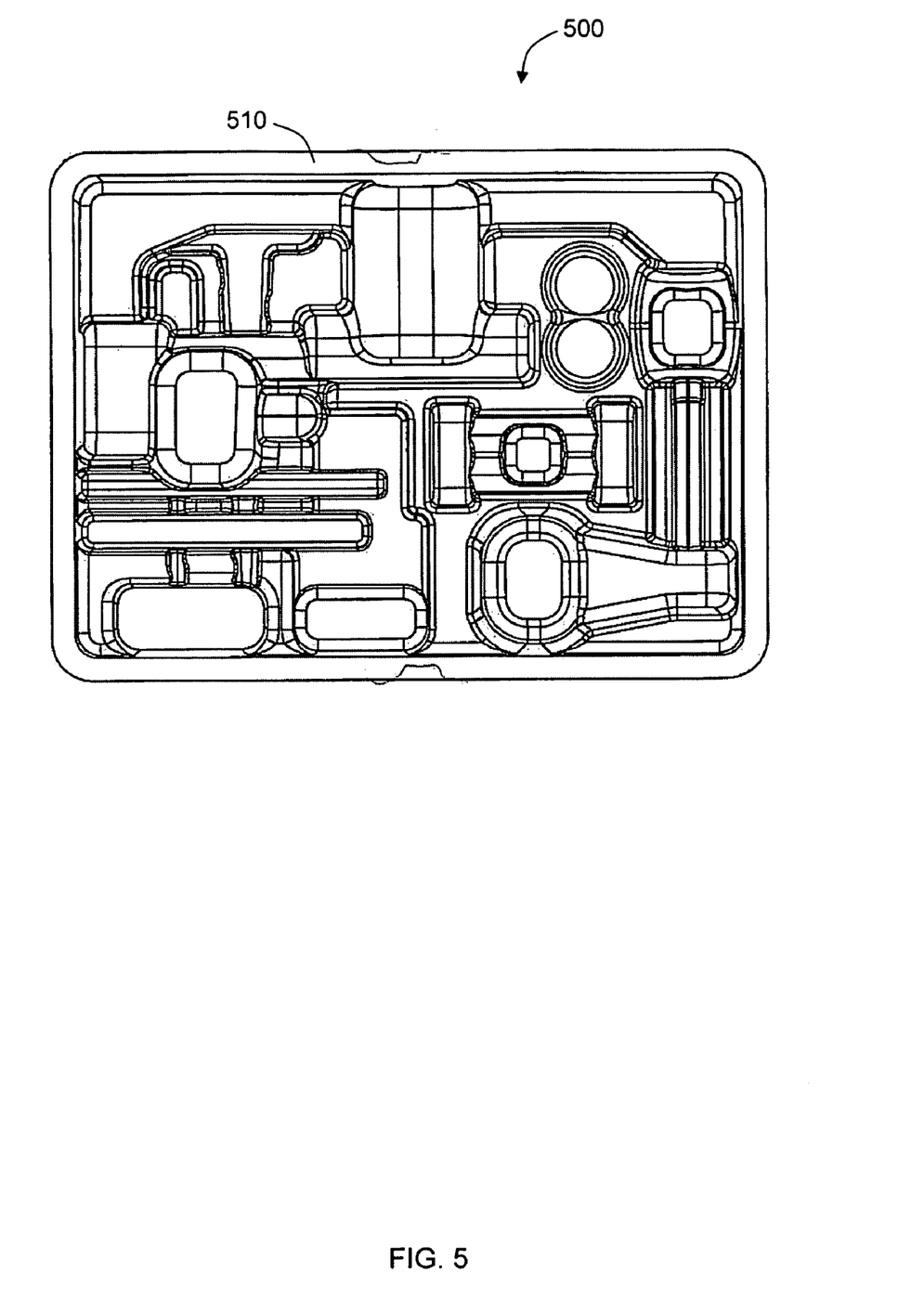
FIG. 5 is an exemplary top view of an inner tray.
Figure 6:
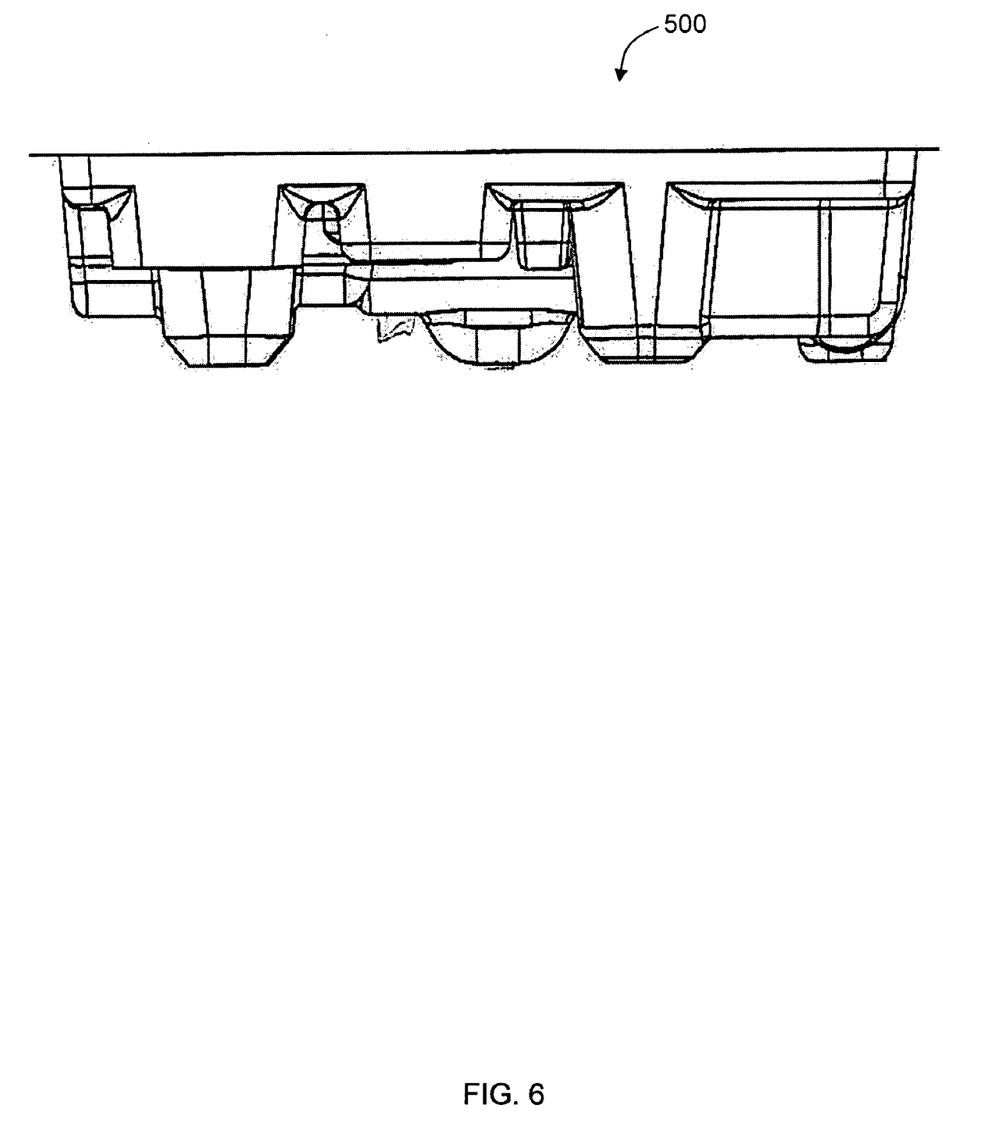
FIG. 6 is an exemplary side view of the inner tray shown in FIG. 5.

FIG. 5 is a top view of an inner tray 500. FIG. 6 is a side view of the inner tray 500 shown in FIG. 5. In the example shown, the inner tray 500 is configured to hold a plurality of medical instruments. The inner tray 500 may have an upper flange or rim 510 that is substantially flat and smooth. In one example, the upper rim 510 may have a width of approximately 9.5 mm. Other rim sizes may be used.

The inner tray 500 may be manufactured from plastic, rubber, polyvinyl chloride (PVC), thermoplastic, or other material. The inner tray 500 may be manufactured via a number of manufacturing processes, including injection molding, compression molding, heat bonding, dye cutting, vacuum forming, or other manufacturing processes.

After the formation of the inner tray 500, a number of medical instruments may be positioned within the inner tray 404. The crevices and inner surfaces of the inner tray 500 may hold the medical instruments in place as the medical kit is being moved from place to place. The medical instruments may include syringes, funnels, forceps, sponges, scapples, hammers, tubes, and needles. Other medical instruments may be used.

After the medical instruments are placed inside of the inner tray 404, the inner tray may be wrapped or sealed by medical packaging 404. In one embodiment, the medical packaging is medical-grade paper. Alternatively, the inner tray may be wrapped in plastic, foil, film, sealing, or other types of medical packaging. For instance, the medical packaging may be manufactured from a permeable material that permits a sterilization agent to enter the wrapped inner tray but does not allow bacterial agents or other microorganisms to enter the wrapped inner tray after sterilization.

The handle assembly may then be positioned with respect to the wrapped inner tray 408. The positioning of the handle assembly may include the handle assembly being fastened to the inner tray.

The handle assembly may have an elongated member. The elongated member may be sufficiently flexible such that elongated member may be wrapped around the inner tray. A distal end of the elongated member may be secured to or interconnected with a proximal end of the elongated member. The ends of the elongated member may be secured by connecting male and female members, clips, clamps, ties, tying the ends together, or other fastening devices. Alternatively, the handle assembly may be affixed to the inner tray, such as by an adhesive.

The handle assembly may have a handle or other grip component operable to lift and/or move the inner tray coupled with the elongated member. The handle assembly may be positioned with respect to the inner tray such that the handle may be positioned substantially flat against the surface of the wrapped inner tray. Alternatively, the handle assembly may be positioned in other positions with respect to the inner tray. For instance, the handle assembly may be positioned such that handle is in an upright position with respect to a surface of the wrapped inner tray.

If the handle assembly becomes off center with respect to the inner tray, control of the inner tray during handling may be adversely affected. Accordingly, in one embodiment, the inner tray may have one or more optional notches on an exterior surface. The optional notches may prevent the handle assembly from sliding out of position and/or off center with respect to the inner tray.

Figure 7:
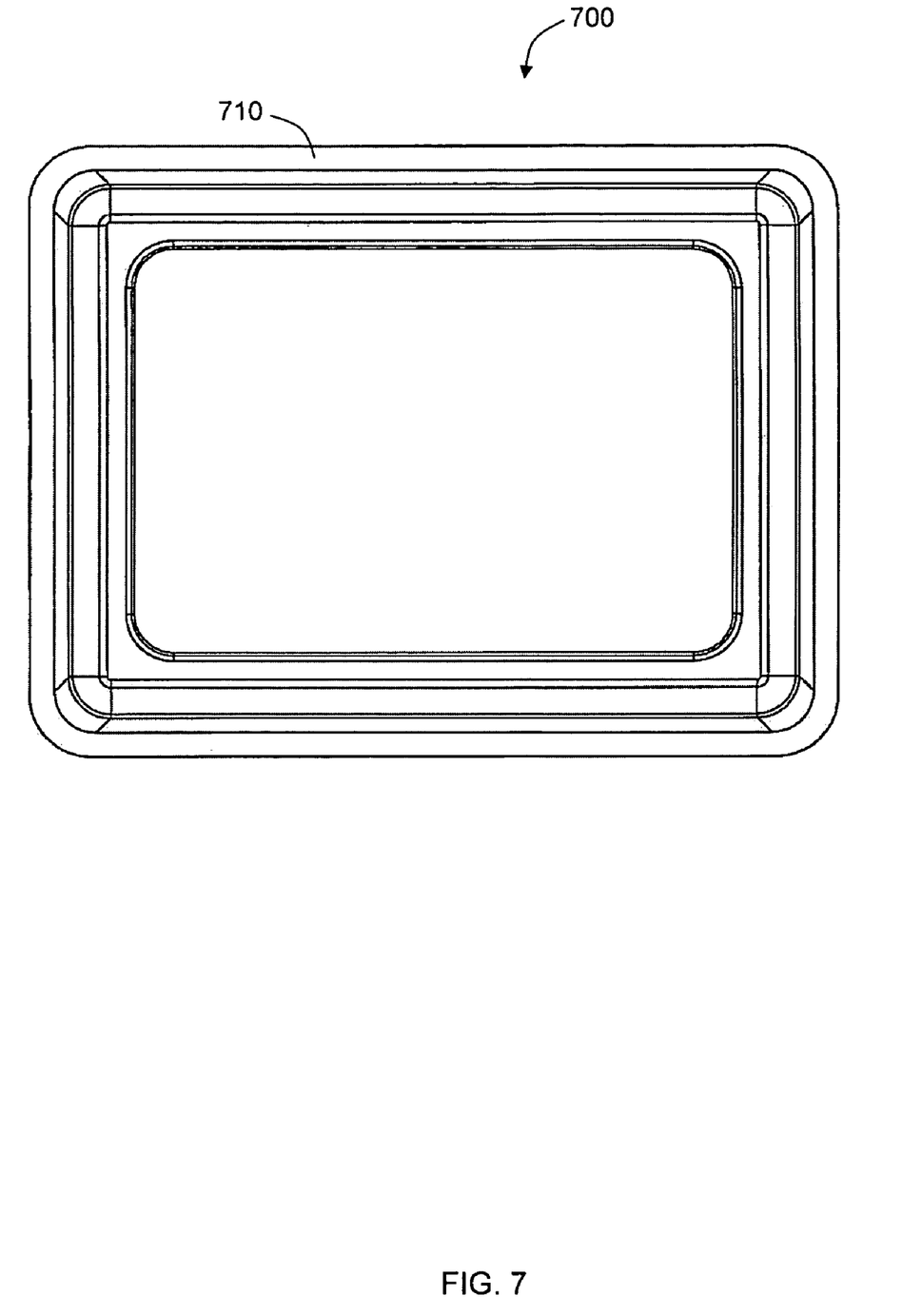
FIG. 7 is an exemplary top view of an outer tray.
Figure 8:
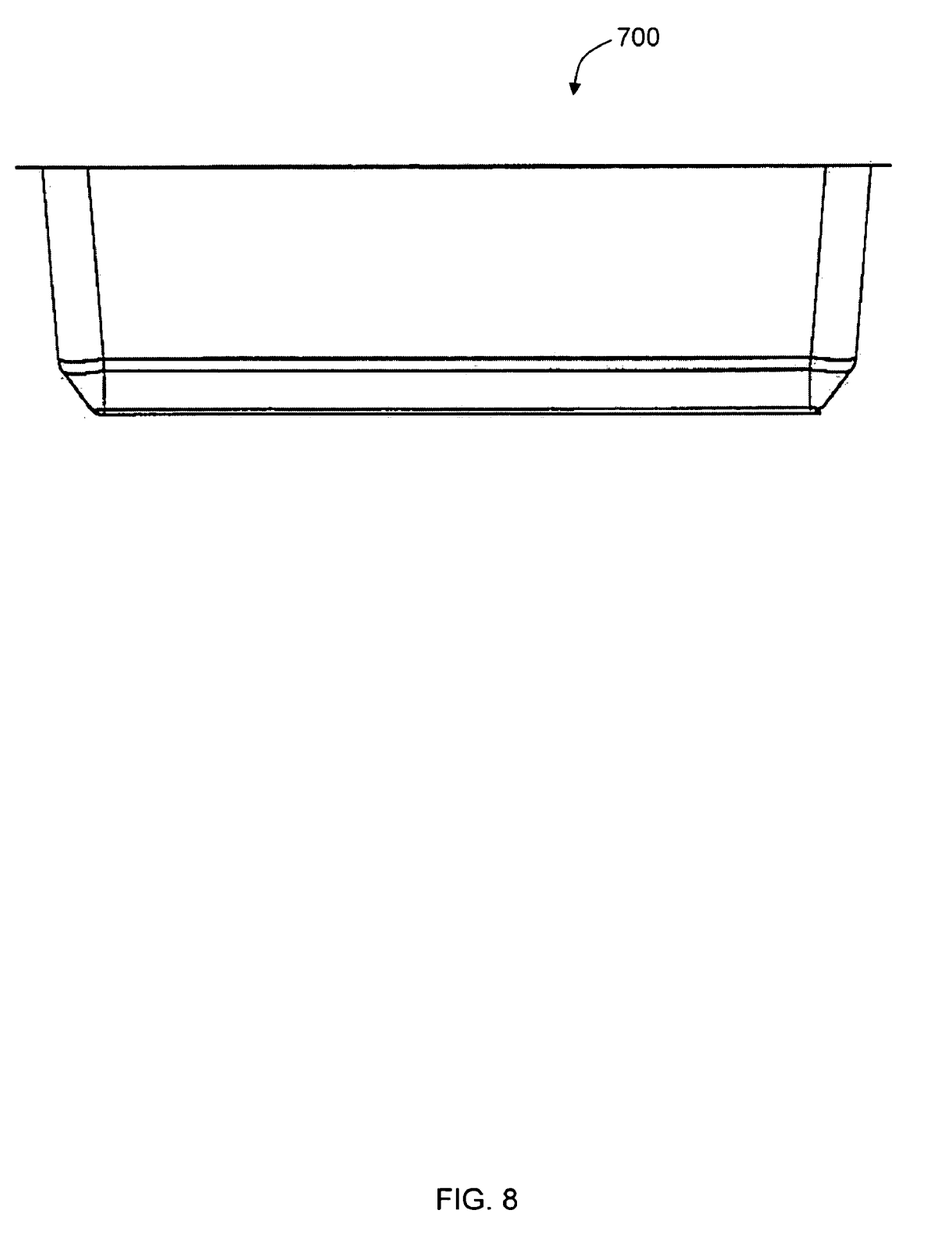
FIG. 8 is an exemplary side view of the outer tray shown in FIG. 7.

After the handle assembly is positioned with respect to the inner tray 408, the inner tray may be set into the outer tray 410. FIGS. 7 and 8 illustrate an exemplary outer tray. The example of FIG. 7 shows a top view of the outer tray 700. The outer tray may have an upper outer rim 710. The upper outer rim 710 may be substantially flat. FIG. 8 shows a side view of the outer tray 700.

The outer tray 700 may be larger than the inner tray. For instance, the outer tray 700 may be longer, wider, and deeper than the inner tray. As such, the inner tray may be placed into the outer tray 700. The inner tray may have an upper inner rim. The upper inner rim may be substantially flat. In one embodiment, the outer tray may be approximately 254 mm wide, approximately 356 mm long, and approximately 76 to approximately 102 mm deep. Other widths, lengths, and depths may be used.

The outer tray 700 may be manufactured from plastic, rubber, polyvinyl chloride (PVC), thermoplastic, or other material. The outer tray 700 may be manufactured via a number of manufacturing processes, including injection molding, compression molding, heat bonding, dye cutting, vacuum forming, or other manufacturing processes.

A bacterial barrier may be formed over the top of the outer tray 412. The bacterial barrier may enclose the inner tray inside of the outer tray. The bacterial barrier may be highly resistant to penetration by bacteria, spores, and other contaminating microorganisms and facilitate the prevention of the contamination of the medical instruments after sterilization. For example, the bacterial barrier may be manufactured from a permeable material that permits a sterilization agent to pass through and sterilize the inner tray and the accompanying medical instruments but also prevents contaminates from reaching and contaminating the inner tray and/or medical instruments.

The bacterial barrier may be stronger than typical medical grade papers, such that resistance to punctures and tears that may contaminate the medical kit is enhanced. The bacterial barrier may generate fewer airborne particulates than medical-grade paper that could contaminate the medical instruments when the medical kit is opened.

The bacterial barrier may be a lid or other seal positioned over the outer tray after the inner tray is placed inside of the outer tray. The lid may enclose everything, such as the inner tray, the medical instruments, and the wrapping paper or other medical packaging, within the outer tray. The lid may be heat bonded to the upper outer rim of the outer tray and/or may be attached to upper outer rim with an adhesive. Alternatively, the lid may snap on and/or over the upper outer rim. The lid may be secured to the outer tray via other manners.

The bacterial barrier may comprise a Tyvek® lid. Tyvek® is made from high density polyethylene fibers (HDPE), which is extremely stable when exposed to sterilizing gases and high-energy sterilization processes. Tyvek® enables sterilizing gases and steam to quickly penetrate and escape.

After the inner tray is sealed or enclosed within the outer tray by the bacterial barrier, a sterilization process may be performed 414 on the medical kit. The sterilization process may sterilize both the inner tray and the accompanying medical instruments. The sterilization process may involve the use of ethylene oxide (EtO), gamma, electron-beam, steam, and plasma/hydrogen peroxide sterilization agents. Other sterilization processes and agents may be used.

The sterilization method may involve the use of ethylene oxide (EtO) gas. The EtO sterilization method may have four primary phases: (1) air removal, (2) steam injection, (3) EtO injection, and (4) gas purge. An EtO sterilization method may be designed for almost every type of permeable packaging kit. The important parameters taken into consideration during the design of an EtO sterilization method typically include temperature, pressure, EtO concentration, gas dwell time, and the instruments being sterilized.

During the EtO sterilization method, EtO may be used to sterilize the inside of the medical kit, including the inner tray and the medical instruments contained therein. The EtO may pass through the bacterial barrier, such as a porous Tyvek® lid. Although sterilization gases such as EtO may penetrate and pass through the bacterial barrier, bacteria and other microorganisms may not. After evacuation of the gases, no new unwanted microorganisms may get inside of the medical kit and the contents of the medical kit remain sterilized.

In use, a circulating nurse may present the medical kit to a sterile nurse during a medical procedure. The circulating nurse may hold the medical kit in one hand and cut or peel away the protective bacterial barrier with the other hand, exposing the inner tray and handling assembly to the sterile nurse. The sterile nurse may lift the inner tray out of the outer tray via the handle of the handle assembly. The sterile nurse may set the inner tray on a table. The sterile nurse may remove the handling assembly and the medical packaging from the inner tray, permitting access to the sterilized medical instruments. The medical packaging may be left in place to provide a sterile area for the inner tray.

Additionally, the outer tray may have an optional grip or handle molded into it, such as either positioned on the side or the bottom of the outer tray, which enhances the control and handling of the medical kit and/or outer tray. The optional grip or handle may facilitate a circulating nurse to hold/control the medical kit with one hand and simultaneously remove the bacterial barrier from the medical kit with the other hand.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

It is therefore intended that the foregoing detailed description be regarded as illustrative rather than limiting, and that it be understood that it is the following claims, including all equivalents, that are intended to define the spirit and scope of this invention.

The invention claimed is:

1. A medical kit containing one or more sterilized medical instruments, the medical kit comprising:
   an outer tray;
   an inner tray containing one or more medical instruments positioned substantially inside of the outer tray; and
   a handle assembly fastened to the inner tray, where the handle assembly comprises a flexible elongated member that is wrapped around the inner tray at a centrally located longitudinal position of the inner tray and then interlocked with itself to maintain a snug fit between the flexible elongated member and corresponding outer surfaces of the inner tray such that substantial slippage of the handle assembly with respect to the inner tray is prevented during use and the handle assembly is operable to facilitate the removal of the inner tray from the outer tray.

2. The medical kit of claim 1, where the handle assembly comprises a handle and the flexible elongated member comprises a male end and a female end and being coupled with the handle, and where the male end is operable to be interconnected with the female end.

3. The medical kit of claim 1, comprising:
   a sheet of medical packaging wrapped around the inner tray, the flexible elongated member being wrapped around both the inner tray and the sheet of medical packaging that is wrapped around the inner tray; and
   a bacterial barrier formed over a portion of the outer tray to enclose the inner tray and the flexible elongated member, where the handle is positioned between the sheet of medical packaging and the bacterial barrier.

4. The medical kit of claim 3, wherein the bacterial barrier is permeable such that the medical instruments in the inner tray may be sterilized via a sterilization process after the bacterial barrier is formed over the portion of the outer tray.

5. The medical kit of claim 3, where the sheet of medical packaging comprises medical-grade paper and the bacterial barrier is manufactured from high density polyethylene fibers.

6. The medical kit of claim 1, where the handle may be positioned to be approximately flush with the inner tray, the handle comprising an annular gripping component that facilitates one-handed lifting of the inner tray from inside of the outer tray.

7. The medical kit of claim 1, where the inner tray is configured to have at least one notch operable to hold the handle assembly in place with respect to the inner tray.

8. The medical kit of claim 1, where the outer tray has an inner vertical wall surface and the inner tray has an upper rim, such that substantially no clearance exists between the first upper rim and the inner vertical wall surface after the inner tray is placed inside of the outer tray.

9. The medical kit of claim 1, where an outer surface of the outer tray is configured to have a grip that facilitates handling the outer tray with one hand.

10. A handle assembly for a medical kit containing one or more sterilized medical instruments, comprising:
    a handle; and
    an elongated member coupled with the handle, the elongated member being wrapped around an entire circumference of an inner tray of the medical kit in which the one or more sterilized medical instruments are positioned, the elongated member being manufactured from flexible material and having a male end and a female end, where the male end is operable to be interconnected with the female end to maintain a snug fit between the elongated member and corresponding surfaces of the inner tray such that substantial slippage of the handle assembly with respect to the inner tray is prevented during use, and where the handle is operable to facilitate the removal of the inner tray in which the one or more sterilized medical instruments are positioned from the medical kit.

11. The handle assembly of claim 10, where the inner tray of the medical kit is covered by a sheet of medical packaging and comprises inner surfaces configured to hold the one or more medical instruments in place as the medical kit is being moved, the elongated member being wrapped around both the entire circumference of the inner tray and the sheet of medical packaging covering the inner tray.

12. The handle assembly of claim 10, where the handle assembly is manufactured from PETG.

13. The handle assembly of claim 10, where the handle is operable to be positioned between a sheet of medical packaging covering an inner tray of the medical kit and a bacterial barrier positioned over a portion of an outer tray of the medical kit to enclose the inner tray.

14. The handle assembly of claim 10, wherein the elongated member is adapted to fit into at least one notch on the medical kit.

15. A method of assembling a medical kit, the method comprising:
   positioning one or more medical instruments in an inner tray;
   fastening a handle assembly, having a handle and an elongated member, to the inner tray by wrapping the elongated member around the inner tray at a centrally located position and then interlocking the handle assembly with itself to maintain a snug fit between the elongated member and corresponding surfaces of the inner tray such that substantial slippage of the handle assembly with respect to the inner tray is prevented during use; and
   positioning the inner tray substantially inside of an outer tray, where the handle is operable to facilitate the removal of the inner tray from the outer tray.

16. The method of claim 15, comprising interconnecting a male end of an elongated member of the handle assembly with a female end of the elongated member of the handle assembly to interlock the handle assembly with itself.

17. The method of claim 15, comprising forming at least one notch on either the inner or the outer tray operable to secure the location of the handle assembly with respect to the medical kit.

18. The method of claim 15, comprising forming a grip on an outer surface of the outer tray to facilitate handling the medical kit with one hand.

19. The method of claim 15, comprising wrapping the inner tray with a sheet of medical packaging before fastening the handle assembly to the inner tray such that the elongated member is wrapped around both the inner tray and the sheet of medical packaging.

20. The method of claim 15, comprising:
   forming a bacterial barrier over a portion of the outer tray to enclose the inner tray after positioning the inner tray substantially inside of the outer tray, the bacterial barrier being manufactured from a permeable material; and
   sterilizing the medical instruments in the inner tray.

* * * * *